US012790581B2

(12) United States Patent
Sun et al.

(10) Patent No.: US 12,790,581 B2
(45) Date of Patent: Nov. 10, 2026

(54) MARINE FUNGUS AND APPLICATION THEREOF

(71) Applicant: INSTITUTE OF OCEANOLOGY, CHINESE ACADEMY OF SCIENCES, Qingdao (CN)

(72) Inventors: Chaomin Sun, Qingdao (CN); Rongrong Gao, Qingdao (CN); Fan Fei, Qingdao (CN); Rui Liu, Qingdao (CN)

(73) Assignee: INSTITUTE OF OCEANOLOGY, CHINESE ACADEMY OF SCIENCES, Qingdao (CN)

( * ) Notice: Subject to any disclaimer, the term of this patent is extended or adjusted under 35 U.S.C. 154(b) by 253 days.

(21) Appl. No.: 18/590,561

(22) Filed: Feb. 28, 2024

(65) Prior Publication Data

US 2024/0254433 A1 Aug. 1, 2024

Related U.S. Application Data

(63) Continuation-in-part of application No. PCT/CN2022/098055, filed on Jun. 10, 2022.

(30) Foreign Application Priority Data

Aug. 30, 2021 (CN) ......................... 202111002458.7

(51) Int. Cl.
*C12N 1/14* (2026.01)
*C12P 7/40* (2006.01)

(52) U.S. Cl.
CPC . *C12N 1/14* (2013.01); *C12P 7/40* (2013.01)

(58) Field of Classification Search
CPC .. C12N 1/00; C12N 1/145; C12N 1/14; C12P 1/02; C12P 7/40
See application file for complete search history.

(56) References Cited

U.S. PATENT DOCUMENTS

| | | | | |
|---|---|---|---|---|
| 2015/0247018 | A1 | 9/2015 | Yang et al. | |
| 2018/0208959 | A1 | 7/2018 | Liu et al. | |
| 2024/0254433 | A1 * | 8/2024 | Sun | C12N 1/205 |

FOREIGN PATENT DOCUMENTS

| | | | |
|---|---|---|---|
| CN | 112522158 | A | 3/2021 |
| JP | 2008237212 | A | 10/2008 |
| WO | 2020177175 | A1 | 9/2020 |

OTHER PUBLICATIONS

Barnes, David K. A. et al., "Accumulation and fragmentation of plastic debris in global environments", Philosophical Transactions of the Royal Society B—Biological Sciences, vol. 364; Year: 2009; pp. 1985-1998.
Danso, Dominik et al., "Plastics: Environmental and Biotechnological Perspectives on Microbial Degradation", Applied and Environmental Microbiology, vol. 85, Issue 19, e01095-19; Published Sep. 17, 2019; pp. 1-14.
Geyer, Roland et al. "Production, use, and fate of all plastics ever made", Science Advances, vol. 3, e1700782; Jul. 19, 2017; pp. 1-5.
Li, W.C. et al.; "Plastic waste in the marine environment: A review of sources, occurrence and effects", Science of the Total Environment, vol. 566-567; Available Online May 24, 2016; pp. 333-349.
Rhodes, Christopher J. ; "Plastic pollution and potential solutions", Science Progress—UK, vol. 101; Published Online Jul. 19, 2018; pp. 207-260.
Rhodes, Christopher J., "Solving the plastic problem:From cradle to grave,to reincarnation", Science Progress—UK, vol. 102(3); Year: 2019; pp. 218-248.

* cited by examiner

*Primary Examiner* — Tekchand Saidha
(74) *Attorney, Agent, or Firm* — NKL Law; Allen Xue

(57) ABSTRACT

A marine-origin fungus is effective in degrading plastic waste. The marine fungus is of fungal strain *Alternaria alternata* FB1. The fungal strain can colonize and grow on polyethylene terephthalate and polyethylene plastics and shows good degradability in polyethylene terephthalate, polyethylene, polyester polyurethane, polyether polyurethane, polypropylene, polystyrene, and several common biodegradable plastics.

6 Claims, 7 Drawing Sheets

Specification includes a Sequence Listing.

MARINE FUNGUS AND APPLICATION THEREOF

INCORPORATION OF SEQUENCE LISTING

This application contains a sequence listing submitted in Computer Readable Form (CRF). The CFR file contains the sequence listing entitled "PA1310182-Sequence-Listing.xml", which was created on Feb. 28, 2024, and is 2,938 bytes in size. The information in the sequence listing is incorporated herein by reference in its entirety.

Technology Field

This invention, a marine-derived fungus and its application in degrading plastic waste, belongs to the field of biotechnology.

Technology Background

Plastics are a class of synthetic materials mainly consisting of polymers derived from petrochemicals (e.g., ethylene, propylene, and vinyl chloride) [1]. Since plastic materials generally have the characteristics of chemical resistance, good insulation, light weight, cheapness, low manufacturing cost, and convenient use, they have brought great convenience to human life and are widely used in construction, machinery, agriculture, food packaging, and other fields involve all aspects of human life. Over the past half-century, plastic has become one of the most used commodities in daily life and an essential part of modern society. However, conventional plastics have extremely high molecular weight and strong hydrophobicity, and lack functional groups recognized by microbial enzyme systems, which makes plastic waste take hundreds of years to be degraded in nature [2]. In addition, a large amount of plastic waste has not been reasonably disposed of, resulting in the accumulation of plastic waste in the environment, which has caused serious "white pollution" to the environment. Plastic pollution has become a major global environmental problem alongside global climate change, ozone depletion, acid rain, etc. According to statistics, by 2015, humans produced a total of 8.3 billion tons of plastic, of which 6.3 billion tons have become garbage. Of the plastic that becomes garbage, only 9% is recycled, 12% is incinerated, and 79% is landfilled or abandoned in the environment. If the current trend continues until 2050, there will be 12 billion tons of plastic waste in landfills and the environment [3]. Taking the ocean as an example, with the progress of human social production and industrial development, the amount of plastic waste entering the ocean every year has increased from about 45,000 tons in 1975 to more than 8 million tons, accounting for 80% of global marine waste [4]. At present, incineration, landfill, and recycling are the main methods adopted to deal with waste plastic pollution. However, landfills not only occupy scarce land resources but also cause secondary pollution. Incineration produces large amounts of toxic gases, and the recycling of plastics is technically demanding and economically inefficient. A further issue that should be considered is to truly achieve biodegradation, especially the degradation of non-degradable plastic products of petroleum origin. Microbial methods of degrading plastics are rather green and environmental protection compared to traditional treatment methods [3, 5, 6]. The development of microbial plastic degradation technology is more realistic and ecologically significant than the traditional ways, whose essence is the result of the action of enzymes secreted by microorganisms.

The degradation begins when microbes contact with the plastic and form biofilm on the plastic surface. Then plastic pores are enlarged by the action of extracellular enzymes and/or compounds released into the extracellular space thus changing the physicochemical properties of the plastic [2]. At present, although a variety of microorganisms that can degrade plastics have been screened out, including fungi, bacteria, and actinomycetes, the degradation efficiency is limited and far from industrial application. At the same time, further research on their mechanism of action is still needed. In-depth research, especially its application, requires further expansion and industrialization. Therefore, it is imperative to screen microorganisms with the ability to efficiently degrade plastics and realize the industrialization of plastic microbial degradation. Bioremediation of plastic waste is an important area worthy of attention in the future.

REFERENCE

[1] D. K. A. Barnes, F. Galgani, R. C. Thompson, M. Barlaz, Accumulation and fragmentation of plastic debris in global environments, Philosophical Transactions of the Royal Society B-Biological Sciences, 364 (2009) 1985-1998.

[2] D. Danso, J. Chow, W. R. Streit, Plastics: Environmental and Biotechnological Perspectives on Microbial Degradation, Applied and Environmental Microbiology, 85 (2019).

[3] R. Geyer, J. R. Jambeck, K. L. Law, Production, use, and fate of all plastics ever made, Science Advances, 3 (2017).

[4] W. C. Li, H. F. Tse, L. Fok, Plastic waste in the marine environment: A review of sources, occurrence and effects, Science of the Total Environment, 566 (2016) 333-349.

[5] C. J. Rhodes, Plastic pollution and potential solutions, Sci Progress-Uk, 101 (2018) 207-260.

[6] C. J. Rhodes, Solving the plastic problem: From cradle to grave, to reincarnation, Sci Progress-Uk, 102 (2019) 218-248.

Contents of the Invention

The purpose of the present invention is to provide a marine-derived fungus and its application in the remediation of plastic-polluted environments.

In order to achieve the above objects, the technical solutions adopted by the present invention are: A marine fungus, characterized in that: the marine fungus is *Alternaria alternata* FB1. The strain is preserved in the Guangdong Provincial Microbial Culture Collection Center. The address is 5th Floor, Building 59, Courtyard, No. 100 Xianlie Middle Road, Guangzhou City, and the preservation date is Jul. 7, 2021, with the collection number GDMCC No:61788.

Application of the marine fungus, i.e. the marine fungus adopted in degrading plastic pollutants in the environment.

The application of the bioactive substances produced by the marine fungus, genetically modified strains using this strain as the starting strain, or the bioactive substances produced by the genetically modified strains using this strain as the starting strain, in degrading plastic pollutants in the environment.

The plastics are polyethylene terephthalate (PET), polyethylene (PE), polyester polyurethane (PAUR), polyether polyurethane (PEUR), polypropylene (PP), polystyrene (PS), one or more of the common biodegradable plastics.

The common biodegradable plastics include one or more types of poly(butylene adipate-co-terephthalate) (PBAT), polybutylene adipate (PBA), polylactic acid (PLA), starch (St), and corn base. Furthermore, several common biodegradable plastics are the biodegradable plastics mixed with poly(butylene adipate-co-terephthalate), polylactic acid and starch (PBAT+PLA+St), the biodegradable plastics mixed with poly(butylene adipate-co-terephthalate) and polylactic acid (PBAT+PLA), the biodegradable plastics mixed with poly(butylene adipate-co-terephthalate), polylactic acid and corn base (PBA+PLA+corn-base).

The microbial inoculant for degrading plastics, which contains one or several following strains or substances, including the fungal strain, the genetically modified strain derived from this strain, the bioactive substances of the strain, and the bioactive substance of the genetically modified strain derived from this strain.

The microbial inoculant contains the culture fluid, the concentrate of culture fluid, or suspension of the cultured fungal strain.

The microbial inoculant culture fluid is made by the strain or genetically modified strain derived from the fungal strain in a culture medium (the culture medium is PDB liquid culture medium) and cultivating it at 30° C. for 2-3 days.

An application of the microbial inoculant in degrading plastic pollutants.

The plastics are polyethylene terephthalate (PET), polyethylene plastic (PE), polyester polyurethane (PAUR), polyether polyurethane (PEUR), polypropylene (PP), polystyrene (PS), one or more of the common biodegradable plastics.

When the microbial inoculant is applied to polyethylene plastic, the surface of the PE plastic is eroded (such as holes appearing), the hydrophilicity of the PE plastic is enhanced, and the molecular weight and crystallinity of the PE plastic are reduced.

When the microbial inoculant is applied to polyethylene terephthalate plastic, the surface of the PET plastic is eroded (such as holes appearing), the hydrophilicity of the PET plastic is enhanced, and the molecular weight and crystallinity of the PET plastic are reduced.

When the microbial inoculant is applied to polypropylene plastic, the surface of the PP plastic is corroded (such as holes appearing).

When the microbial inoculant is applied to polystyrene plastic, the surface of the PS plastic is corroded (such as holes appearing).

When the microbial inoculant is applied to polyester-type polyurethane plastic, the PAUR plastic is corroded (such as holes and/or cracks appearing).

When the microbial inoculant is applied to polyether-type polyurethane plastic, the surface of the PEUR plastic is corroded (such as holes appearing).

When the microbial inoculant is applied to several common biodegradable plastics: PBAT+PLA+St plastic, PBAT+PLA plastic, and PBA+PLA+corn-base plastic, these plastics are corroded (such as holes and/or cracks appearing).

Advantages of the Present Invention

The marine fungus in the present invention is isolated from the intertidal zone of Qingdao bathing beach and belongs to filamentous fungi. The sterile hyphae are creeping and separated, and the conidiophores are solitary or clustered. Most are unbranched, short, and almost indistinguishable from vegetative hyphae. The conidium is inverted rod-shaped, its tip lengthened into a pale brown beak, with dark brown brick-like partitions, and a constant number of them are in chains. It is a common saprophytic fungus in soil and air. This strain can efficiently degrade polyethylene terephthalate, polyethylene, polyester polyurethane, polyether polyurethane, polypropylene, polystyrene, and several common biodegradable plastics. It has potential application value in terms of developing microbial inoculants for environmental remediation and improving the ecological environment. At the same time, mixing it with other strains also has a certain effect on the degradation of plastics.

Compared with traditional plastic pollutant treatment methods, microbial degradation also has potential application value in solving the problem of "White Pollution".

MODE OF CARRYING OUT THE INVENTION

The present invention will be further described below regarding specific examples. These examples are only used to illustrate the invention and are not intended to limit the scope of the invention.

Example 1

Isolation and identification of a marine derived fungus, *Alternaria alternata*: In mid-to-late July 2017, sediments with plastic garbage were collected from the intertidal zone of Qingdao No. 1 Bathing Beach. The samples contained beverage bottles (PET), fast food packaging boxes (PET and PE), plastic wrap (PE), and other plastic debris fragments and surrounding soil sediments, a total of 300 samples.

Sterile seawater with PET and PE plastics was the screening medium. The 300 samples collected were placed in the screening medium to screen plastic-degrading microorganisms at room temperature. After six months of screening, a strain that could effectively colonize two types of plastics and have a degradation effect was finally obtained. According to its morphological observation, it may be a fungus. The strain was further isolated and cultured on PDA medium in a 30° C. constant temperature incubator to obtain pure colonies and preserve the strains.

PDA medium components: 200 g potatoes, 20 g glucose, 15-20 g agar, 1 L water, pH 7.5.

The fungus was identified by ITS. Through comparison, it was found that the fungus was *Alternaria alternata*, with an identity of 99.81%.

Its ITS sequence is:

```
>Alternaria alternata FBI
SEQ ID NO: 1:
GCTGGGATTTGAGGCGGGCTGGACCTCTCGGGGTTACAGCCTTGCTGAA

TTATTCACCCTTGTCTTTTGCGTACTTCTTGTTTCCTTGGTGGGTTCGC

CCACCACTAGGACAAACATAAACCTTTTGTAATTGCAATCAGCGTCAGT

AACAAATTAATAATTACAACTTTCAACAACGGATCTCTTGGTTCTGGCA

TCGATGAAGAACGCAGCGAAATGCGATAAGTAGTGTGAATTGCAGAATT

CAGTGAATCATCGAATCTTTGAACGCACATTGCGCCCTTTGGTATTCCA

AAGGGCATGCCTGTTCGAGCGTCATTTGTACCCTCAAGCTTTGCTTGGT

GTTGGGCGTCTTGTCTCTAGCTTTGCTGGAGACTCGCCTTAAAGTAATT

GGCAGCCGGCCTACTGGTTTCGGAGCGCAGCACAAGTCGCACTCTCTAT

CAGCAAAGGTCTAGCATCCATTAAGCCTTTTTTTCAACTTTTGACCTCG

GATCAGGTAGGGATACCCGCTGAACTTAAGCATATCAAAAGGCGGGAGG
```

-continued

```
AATTTTTCTTCTTGG
```

The preservation information of the above strains is as follows:

Strain name: *Alternaria alternata* FB1;
Preservation institution: Guangdong Microbial Culture Collection Center (GDMCC);
Address: 5th Floor, Building 59, No. 100 Xianlie Middle Road, Guangzhou, China;
Storage date: Jul. 7, 2021;
Deposit number: GDMCC No: 61788.

Example 2

Preparation of the Fugal Inoculant:

The strain *Alternaria alternata* obtained in the above embodiment was inoculated into PDB liquid medium (200 g potatos, 20 g glucose, 1 L water, pH 7.5) and cultured at 30° C. for 2 days. The resulting microbial suspension was obtained as the fungal inoculant.

Figure 1:
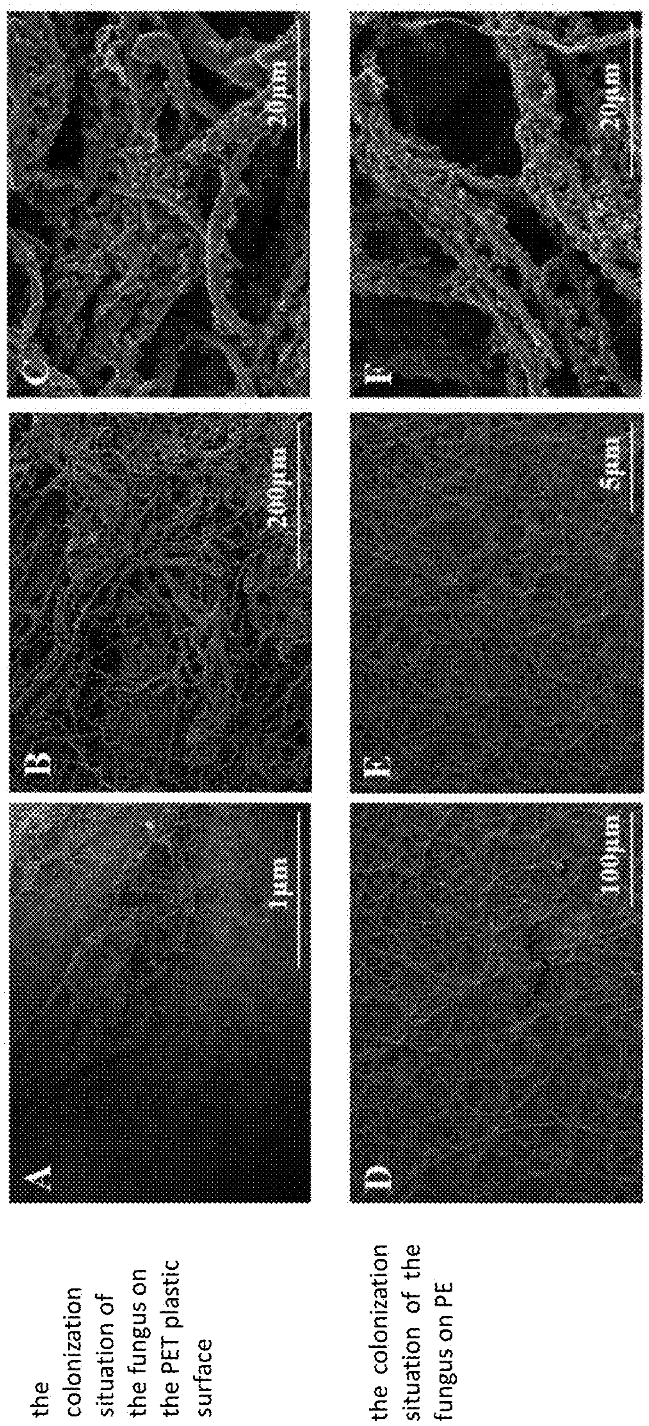
FIG. 1. The colonization situation of the marine fungus on the surface of polyethylene terephthalate and polyethylene plastic. Panels A-C, the colonization situation of the fungus on the PET plastic surface. Panels D-F, the colonization situation of the fungus on PE.

Use the fungal inoculant obtained above to degrade plastics:

1) PET and PE plastics were placed at a constant temperature of 30° C. in a basic liquid medium (xylose 0.02 g/L, yeast powder 0.05 g/L, seawater 1 L, pH 7.5) with or without the above-mentioned fugal inoculants in an incubator. After two weeks of cultivation, take a piece of plastic sheet and prepare the biological sample to observe the biofilm colonization on its surface (FIG. 1). Among them, adding 1 mL of the fungal suspension obtained above to IL of the basic liquid medium is a basic liquid culture medium containing fungal inoculants.

Method for preparing biological samples for scanning electron microscopy: wash the plastic sheet containing bacterial biofilm once with 0.1 mol/L PBS (pH7.0), soak the plastic sheet with 5% glutaraldehyde to fix the cells for 1 hour, wash the plastic sheet with sterile PBS, dehydrate with 30%, 50%, 70%, 90%, and 100% graded ethanol for 15 min respectively, and dry with $CO_2$. The material is mounted on the pile and sputter coated with gold and platinum (10 nm) for 5 min using a Hitachi MC1000 ion sputterer, and then observed with a scanning electron microscope (Hitachi S-3400N). The scanning electron microscope observation voltage is 5 kV, the energy spectrum scanning voltage is 5 k eV, and the action time is 30 s.

Observing the colonization effect of fungi on plastics from FIG. 1, it was found that the fungus could colonize well on both plastics and form a dense biofilm.

2) PET and PE plastics were placed at a constant temperature of 30° C. in a basic liquid medium (xylose 0.02 g/L, yeast powder 0.05 g/L, seawater 1 L, pH 7.5) with or without the above-mentioned inoculants in an incubator. PET was co-cultured with the above-mentioned microbial inoculants for two weeks for observation, and PE was co-cultured with the above-mentioned microbial inoculants for 120 days for observation. Take the plastic film and prepare non-biological samples to observe the surface degradation (see FIG. 2 and FIG. 3). Among them, adding 1 ml of the fungal suspension obtained above to IL of the basic liquid medium is a basic liquid culture medium containing microbial inoculants.

Method for preparing non-biological samples for scanning electron microscopy: soak in a 50° C. constant-temperature water bath with 3% hydrogen peroxide for 12 hours, ultrasonically wash with 75% ethanol and distilled water for 30 minutes, and then fully dry. The material was mounted on the pile and sputter coated with gold and platinum (10 nm) for 5 min using a Hitachi MC1000 ion sputterer and observed with a scanning electron microscope (Hitachi S-3400N). The scanning electron microscope observation voltage is 5 kV, the energy spectrum scanning voltage is 5 keV, and the action time is 30 s.

Figure 2:
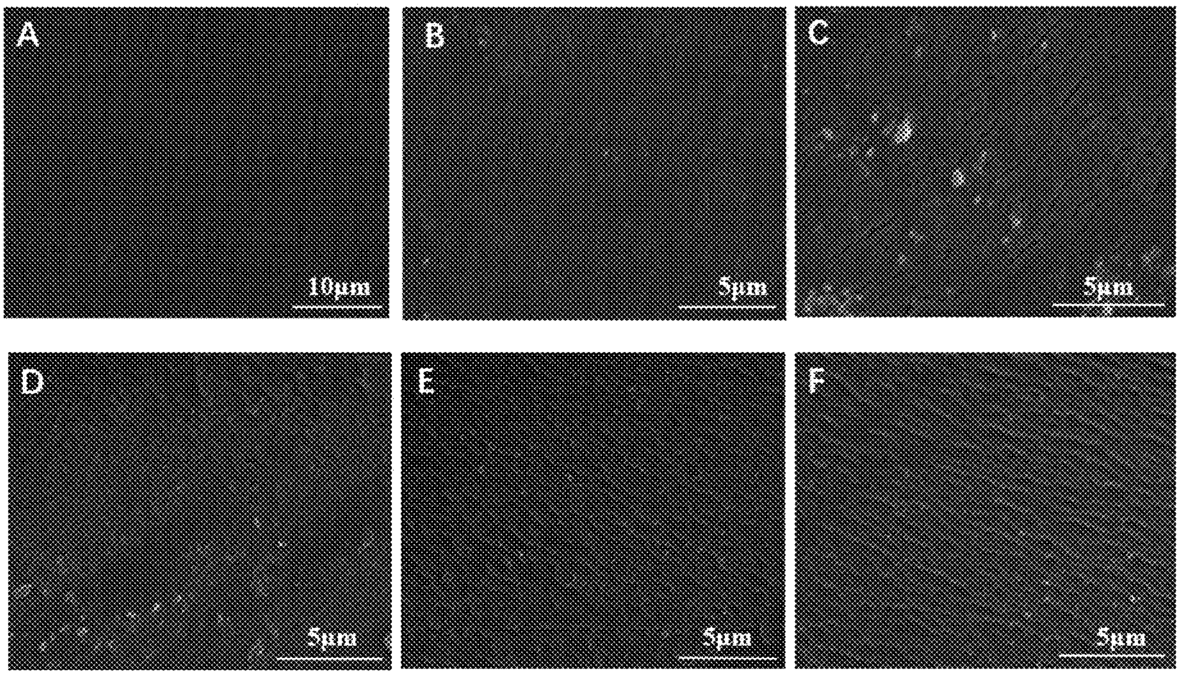
FIG. 2. The surface morphology changes of PET after fungal degradation observed under a scanning electron microscope. Panel A, the control group of PET without microbial inoculant. Panels B-F, the morphological changes of PET plastic after fungal degradation.
Figure 3:
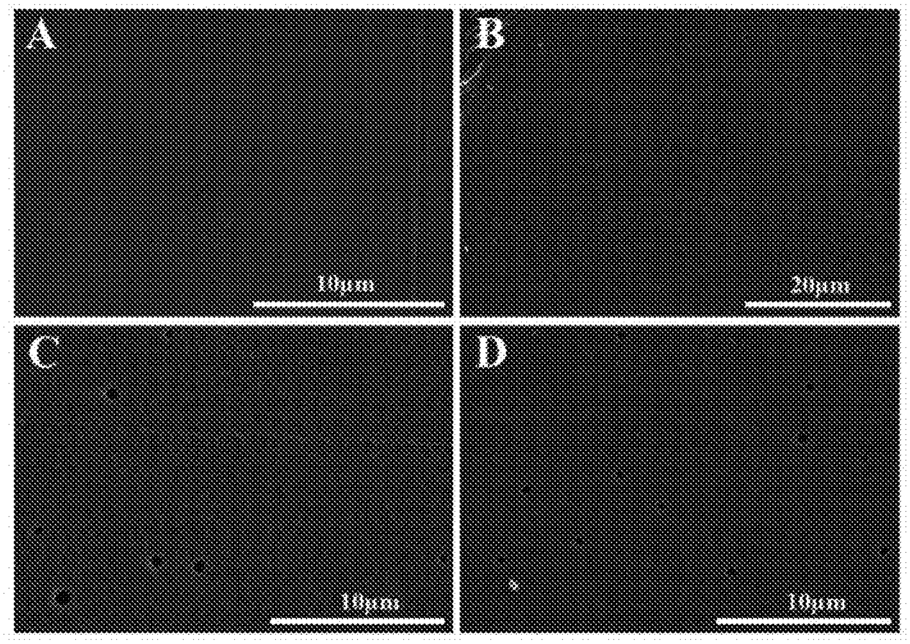
FIG. 3. The surface morphology changes of PE plastic after fungal degradation observed under a scanning electron microscope. Panel A, is the control group of PE without microbial inoculant. Panels B-D, the morphological changes of PE plastic after fungal degradation.

From the electron microscope observation shown in FIGS. 2 and 3, it was found that the surface of the plastic colonized by this fungus was uneven and had holes, which proved that this fungus had good degradation ability for both plastics.

3) Add the microbial inoculant above to the basic liquid medium containing PET or PE plastics. The amount of the inoculant added was about 1 ml of the fungal suspension. After addition, culture for 2 weeks and 4 weeks. The medium without microbial inoculant was defined as the control group. Then the PE and PET plastic film colonized by fungi were washed away from the biofilm for infrared observation (FIG. 4).

The above method of removing biofilm was to clean with 3% hydrogen peroxide, distilled water, and 75% ethanol in an ultrasonic cleaner for 30 minutes. After sufficient drying, the PE or PET film was scanned using a Nicolet-360 FTIR (Waltsam, USA) spectrometer with a wavelength range of 450-4000 $cm^{-1}$ and a resolution of 1 $cm^{-1}$, operating in ATR mode. Thirty-two scans were performed for each spectrum.

Figure 4:
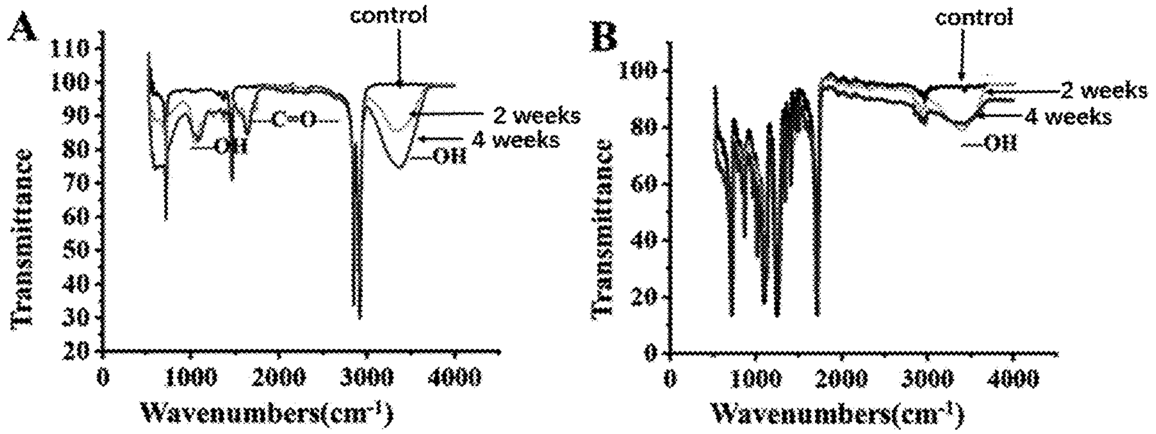
FIG. 4. The Fourier transform infrared (FTIR) spectrometer observation results after the degradation of the microbial inoculant of the present invention. Panel A, the FTIR spectrometer observation result of PE plastic. Panel B, the FTIR spectrometer observation result of PET.

The results in FIG. 4 Panel A show that after two weeks and four weeks of fungal colonization, two extra FTIR spectra absorption peaks of hydroxyl and carbonyl groups were observed, and the peak area increased with the growth of culture time, proving that the hydrophilicity of PE plastic increased and that this microbial inoculant had a degrading effect on PE plastic.

The results in FIG. 4 Panel B show that after two weeks and four weeks of fungal colonization, extra FTIR spectra absorption peak of hydroxyl groups was observed, and the peak area increased with the growth of culture time, proving that the hydrophilicity of PET plastics increased and that this microbial inoculant had a degrading effect on PET plastic.

Figure 5:
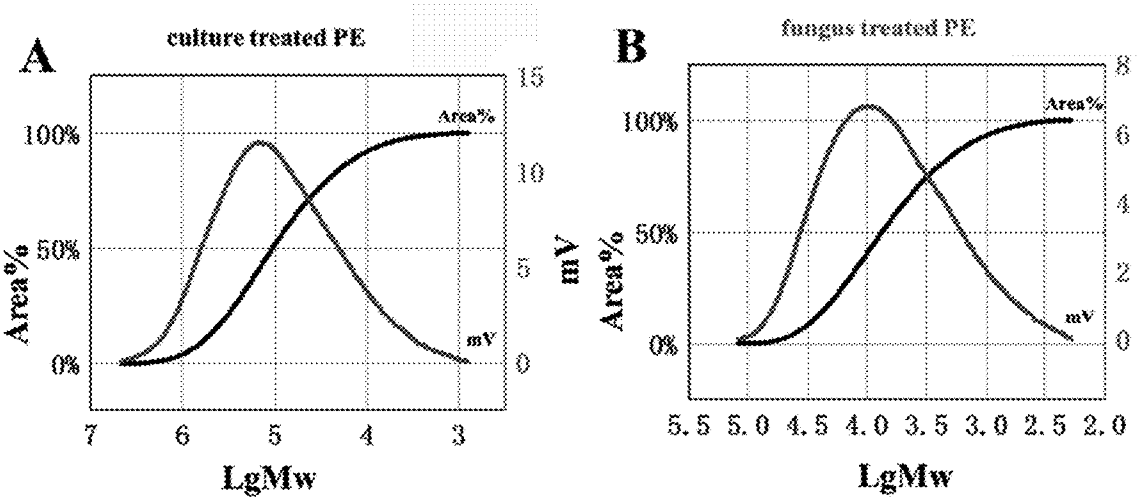
FIG. 5. The results of high-temperature GPC analysis of PE plastic after the degradation of the microbial inoculant of the present invention. Panel A, no inoculant was added. Panel B, the inoculant was added.

4) Add the microbial inoculant above to the basic liquid medium containing PE plastic. The amount of the inoculant added was about 1 ml of the fungal suspension. After addition, culture for 120 days. The medium without microbial inoculant was the control group. Then the plastic treated with the microbial inoculant was analyzed by high-temperature gel chromatography for its degradation ability (FIG. 5). High-temperature gel chromatography analysis of PE plastics used Agilent PL-GPC220 and Agilent PLgel Olexis 300 7.5 mm chromatographic columns. At 150° C., GPC was used to determine the molecular weight of PE films treated with culture media and fungi. After calibration with polystyrene standards of known molecular weight, trichlorobenzene was used as the mobile phase (1 mL/min). The sample concentration was 1 mg/mL.

The results in FIG. 5 show that after treatment with this fungus, the overall number-average molecular weight of PE changed from 29218 to 3223, and the overall molecular weight changed from 231017 to 11959. The high molecular weight area decreased and the low molecular weight area increased. It was proved that this microbial inoculant had a good degradation effect on polyethylene plastic.

Figure 6:
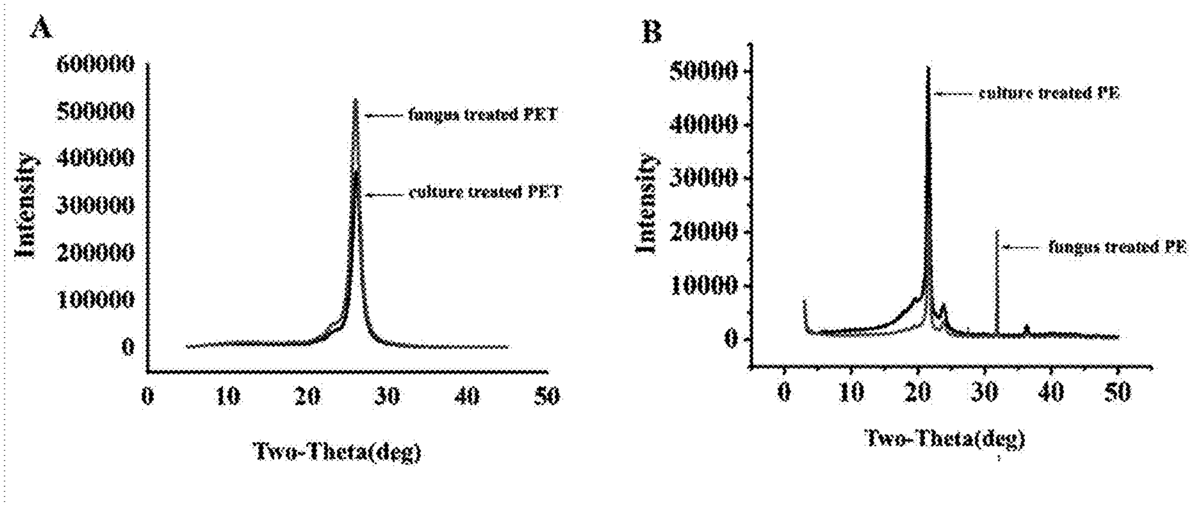
FIG. 6. The X-ray diffraction patterns of PET Panel A and PE plastic Panel B after degradation by the microbial inoculant of the present invention.
Figure 7:
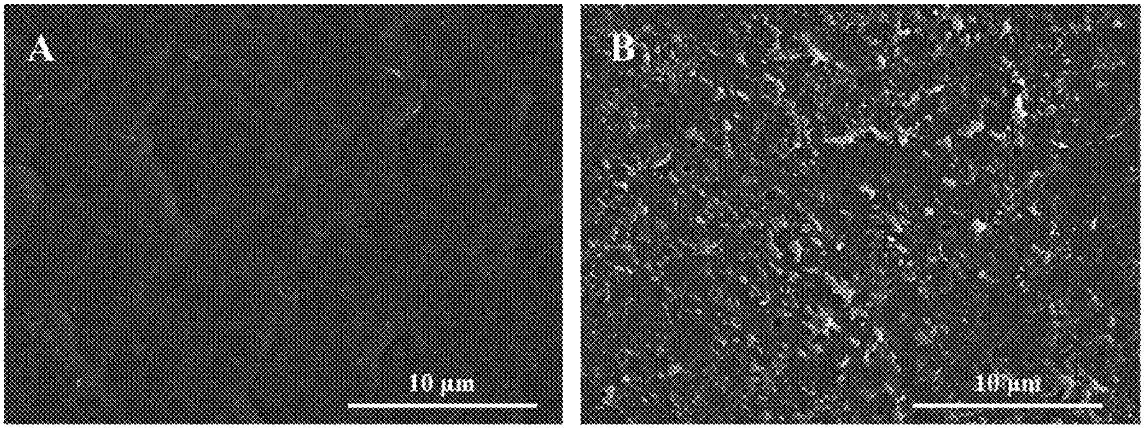
FIG. 7. The surface morphology changes of PP plastic after fungal degradation observed under a scanning electron microscope. Panel A, the control group without microbial inoculant. Panel B, the PP plastic after fungal degradation.
Figure 8:
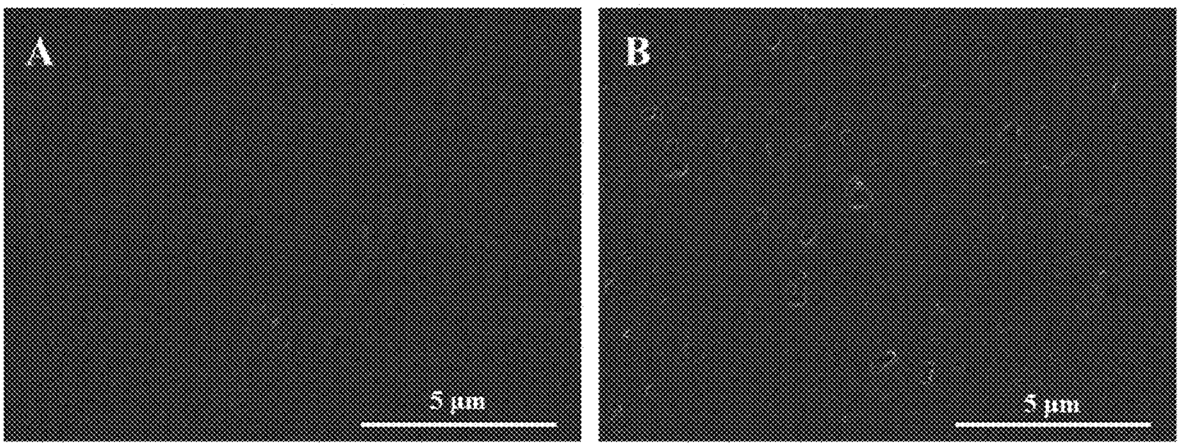
FIG. 8. The surface morphology changes of PS plastic after fungal degradation observed under a scanning electron microscope. Panel A, the control group without microbial inoculant. Panel B, the PS plastic after fungal degradation.

5) Add the microbial inoculant above to the basic liquid medium containing PET or PE plastics. The amount of the inoculant added was about 1 ml of the fungal suspension. After addition, culture for four weeks. The medium without microbial inoculant was the control group. Then the X-ray diffraction pattern of the plastic was used to analyze the degradation ability of the microbial inoculant (FIG. 6). The corresponding instrument was Bruker D8 Advance, the ray was CuKα ray, the tube current was 40 mA, and the tube voltage was 40 kV. PET sample 2θ angle scanning range: 5° to 45°, scanning rate: 1° $min^{-1}$. PE sample 2θ angle scanning range: 3° to 50°, scanning rate: 1° $min^{-1}$.

The results in FIG. 6 show that the relative crystallinity of the PET sample dropped from 71.47% to 70.46%. The relative crystallinity of the PE sample decreased from 62.79% to 52.02%. It was proved that the microbial inoculant had a certain degradation ability for both plastics.

6) Put the four plastics of PP, PS, PAUR, and PEUR into rice medium (rice 700 g/L, yeast powder 5 g/L, peptone 3 g/L, corn steep liquor 2 g/L, MSG 6 g/L, seawater 1 L) with or without the above-mentioned inoculants. After culturing for 30 days in a 30° C. constant-temperature incubator, take out each plastic film and prepare non-biological samples to observe their surface degradation (FIG. 7, FIG. 8, FIG. 10, and FIG. 11). Among them, adding 1 ml of the fungal suspension obtained above to the rice culture medium was the rice culture medium containing the microbial inoculant.

Method for preparing non-biological samples for scanning electron microscopy: After 30 days of culture, take out each plastic film and soak it in a 50° C. constant-temperature water bath with 3% hydrogen peroxide for 24 hours, then ultrasonically wash it with 75% ethanol and distilled water for 30 minutes, and then intensive drying. The material was mounted on the pile and sputter coated with gold and platinum (10 nm) for 5 min using a Hitachi MC1000 ion sputterer. Observe with a scanning electron microscope (Hitachi S-3400N). The scanning electron microscope observation voltage was 5 kV, the energy spectrum scanning voltage was 5 keV, and the action time was 30 s.

From the electron microscope observation in FIGS. 7, 8, 10, and 11, it is found that the surface of the plastic after colonization by this fungus was uneven, with dense cracks or holes, proving that this fungus had good degradability to PP, PS, PAUR, and PEUR plastic.

7) Add the microbial inoculant above to the rice medium containing PAUR plastic. The amount of the inoculant added was about 1 ml of the fungal suspension. After addition, culture for 7 days, 14 days, 21 days, 28 days, and 35 days respectively. The medium without microbial inoculant was the control group. Then the biofilm was washed away from the PAUR membrane colonized by the bacterial inoculant for observation (FIG. 9).

The above method of removing biofilm was to soak in 3% hydrogen peroxide in a constant temperature water bath at 50° C. for 24 hours, and ultrasonically clean with 75% ethanol and distilled water for 30 minutes respectively. After sufficient drying, observe.

Figure 9:
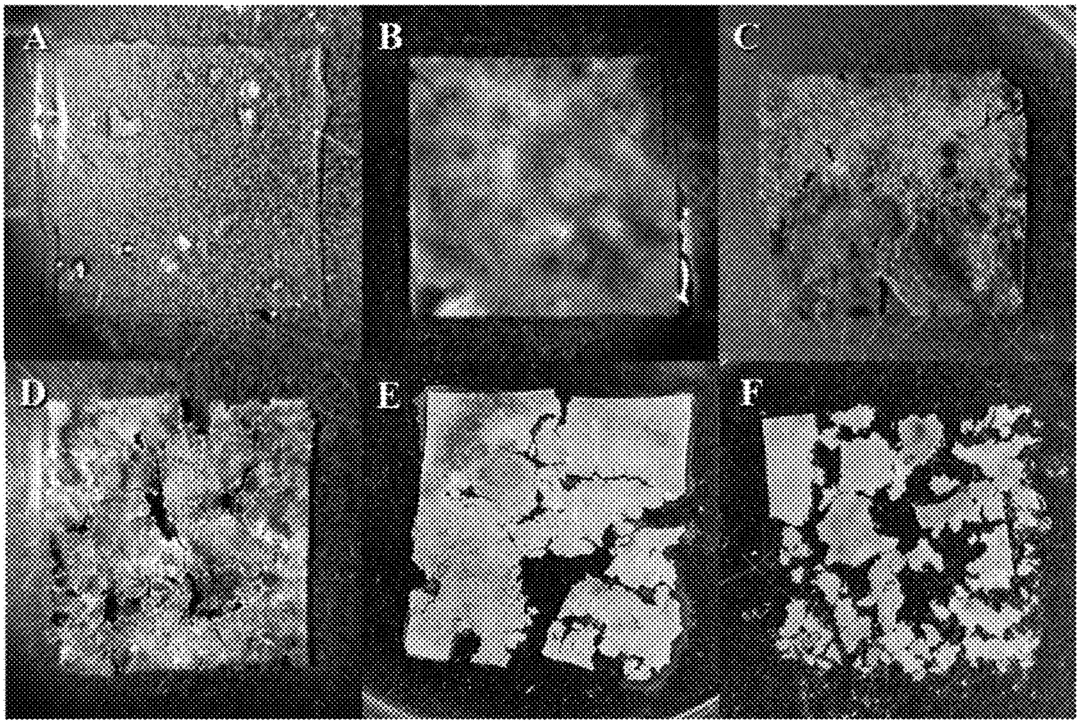
FIG. 9. The morphological changes of the PAUR film after being degraded by the microbial inoculant of the present invention. Panel A, the control group without microbial inoculant. Panel B, the PAUR plastic after 7 days of fungal degradation. Panel C, the PAUR plastic after 14 days of fungal degradation. Panel D, the PAUR plastic after 21 days of fungal degradation. Panel E, the PAUR plastic after 28 days of fungal degradation. Panel F, the PAUR plastic after 35 days of fungal degradation.
Figure 10:
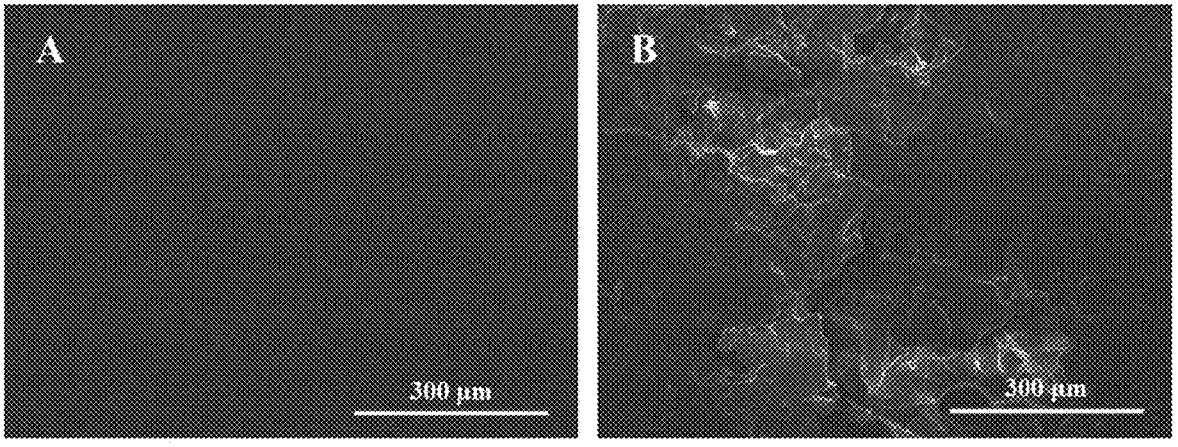
FIG. 10. The surface morphology changes of PAUR after fungal degradation observed under a scanning electron microscope. Panel A, the control group without microbial inoculant. Panel B, the PAUR plastic after fungal degradation.
Figure 11:
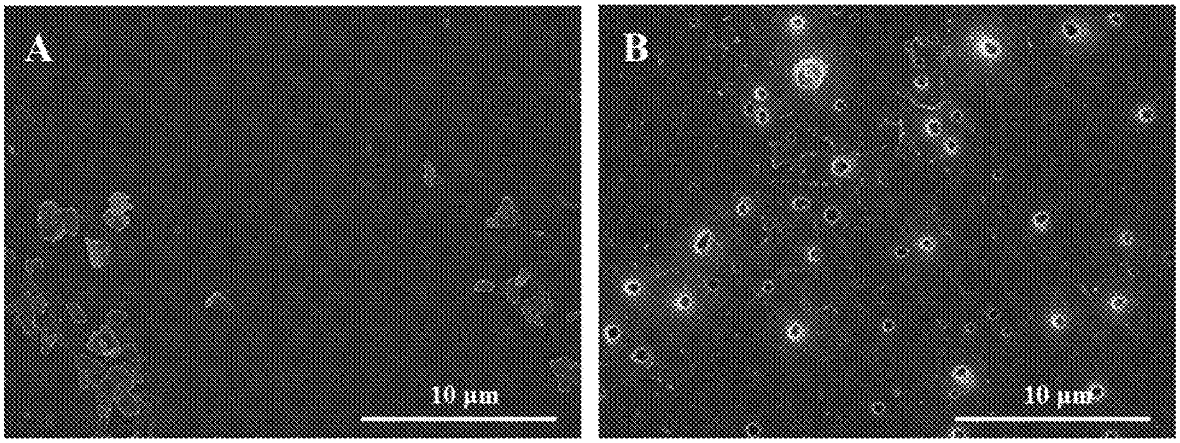
FIG. 11. The surface morphology changes of PEUR after fungal degradation observed under a scanning electron microscope. Panel A, the control group without microbial inoculant. Panel B, the PEUR plastic after fungal degradation.

FIG. 9 shows that, after 14 days of microbial inoculant treatment, cracks appeared on the surface of the PAUR diaphragm. As the treatment time increased, the cracks in the PAUR diaphragm became larger and gradually became fragmented, proving that the microbial inoculant had a good degradation ability of PAUR plastic.

8) Add the inoculants above to the rice medium (rice 700 g/L, yeast powder 5 g/L, peptone 3 g/L, corn steep liquor 2 g/L, monosodium glutamate 6 g/L, seawater 1 L) containing different conventional biodegradable plastics (biodegradable plastics containing poly(butylene adipate-co-terephthalate), polylactic acid and starch (PBAT+PLA+St)), biodegradable plastics containing poly(butylene adipate-co-terephthalate) and polylactic acid (PBAT+PLA), biodegradable plastics containing polybutylene adipate, polylactic acid and corn-base (PBA+PLA+corn-base)). The amount of the inoculant added was about 1 ml of the fungal suspension and cultured for 30 days. The medium without microbial inoculant was the control group. Then different conventional biodegradable plastic films colonized by fungi were washed away and observed (FIG. 12).

The above method of removing biofilm was to soak in 3% hydrogen peroxide in a constant temperature water bath at 50° C. for 12 hours, and ultrasonically clean with 75% ethanol and distilled water for 30 minutes respectively. After sufficient drying, observe.

Figure 12:
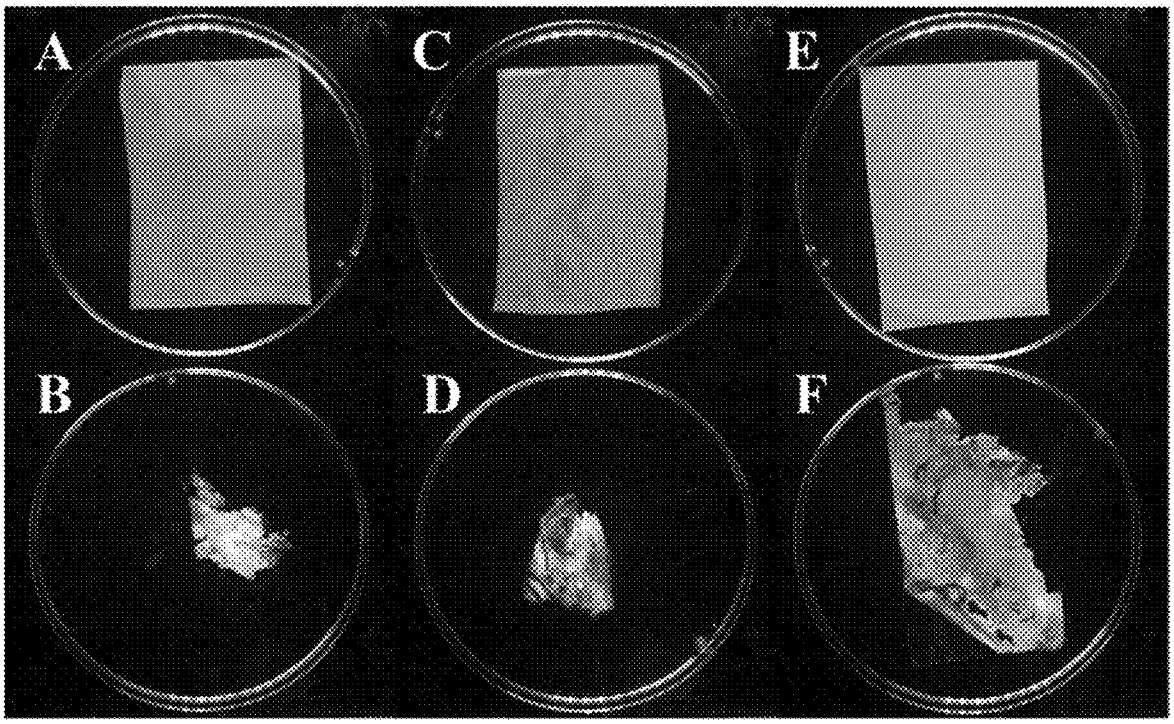
FIG. 12. The morphological changes of several common biodegradable plastics after being degraded by the microbial inoculant of the present invention. Image A, the control group of PBAT+PLA plastic without microbial inoculant. Image B, the PBAT+PLA plastic after fungal degradation. Image C, the control group of PBAT+PLA+St plastic without microbial inoculant. Image D, the PBAT+PLA+St plastic after fungal degradation. Image E, the control group of PBA+PLA+corn-base plastic without microbial inoculant. Image F, the PBA+PLA+corn-base plastic after fungal degradation.

FIG. 12 shows that three biodegradable plastics, PBAT+PLA+St, PBAT+PLA, and PBA+PLA+corn-base, had varying degrees of deterioration after being treated with microbial inoculants for 30 days. All three plastics showed cracks and fragments and had smaller sizes, which proves that the microbial inoculant had a good degradation ability for biodegradable plastics containing one or several ingredients of PBAT, PLA, PBA, St, and corn base.

We claim:

1. A method for degrading a plastic, comprising contacting a biological material with the plastic to be degraded, wherein the biological material is a marine fungus or an active substance produced by the marine fungus, wherein the marine fungus is of fungal strain *Alternaria alternata* FB1, deposited at the Guangdong Provincial Microbial Culture Collection Center, whose address is 5th Floor, Building 59, Courtyard, No. 100 Xianlie Middle Road, Guangzhou City, under the GDMCC Accession No: 61788 on Jul. 7, 2021.

2. The method according to claim 1, wherein the plastic is one or more selected from polyethylene terephthalate (PET), polyethylene (PE), polyester polyurethane (PAUR), polyether polyurethane (PEUR), polypropylene (PP), and polystyrene (PS).

3. The method according to claim 1, wherein the plastic comprises poly(butylene adipate-co-terephthalate) (PBAT), polybutylene adipate (PBA), polylactic acid (PLA), starch (St), or corn base.

4. A method for degrading a plastic, comprising contacting a microbial inoculant with the plastic, wherein the microbial inoculant comprises a marine fungus of fungal strain *Alternaria alternata* FB1, deposited at the Guangdong Provincial Microbial Culture Collection Center, whose address is 5th Floor, Building 59, Courtyard, No. 100 Xianlie Middle Road, Guangzhou City, under the GDMCC Accession No: 61788 on Jul. 7, 2021.

5. The method according to claim 4, wherein the plastic is polyethylene terephthalate (PET), polyethylene (PE), polyester polyurethane (PAUR), polyether polyurethane (PEUR), polypropylene (PP), or polystyrene (PS).

6. The method according to claim 4, wherein the plastic comprises one or more selected from poly(butylene adipate-co-terephthalate) (PBAT), polybutylene adipate (PBA), polylactic acid (PLA), starch (St), and corn base.

* * * * *

SEQUENCE LISTING

```
Sequence total quantity: 1
SEQ ID NO: 1            moltype = DNA  length = 554
FEATURE                 Location/Qualifiers
misc_feature            1..554
                        note = synthesized
source                  1..554
                        mol_type = other DNA
                        organism = synthetic construct
SEQUENCE: 1
gctgggattt gaggcgggct ggacctctcg gggttacagc cttgctgaat tattcaccct  60
tgtcttttgc gtacttcttg tttccttggt gggttcgccc accactagga caaacataaa  120
ccttttgtaa ttgcaatcag cgtcagtaac aaattaataa ttacaacttt caacaacgga  180
tctcttggtt ctggcatcga tgaagaacgc agcgaaatgc gataagtagt gtgaattgca  240
gaattcagtg aatcatcgaa tctttgaacg cacattgcgc cctttggtat tccaaagggc  300
atgcctgttc gagcgtcatt tgtaccctca agctttgctt ggtgttgggc gtcttgtctc  360
tagctttgct ggagactcgc cttaaagtaa ttggcagccg gcctactggt ttcggagcgc  420
agcacaagtc gcactctcta tcagcaaagg tctagcatcc attaagcctt tttttcaact  480
tttgacctcg gatcaggtag ggatacccgc tgaacttaag catatcaaaa ggcgggagga  540
atttttcttc ttgg                                                    554
```